(12) United States Patent
Brown et al.

(10) Patent No.: US 6,981,985 B2
(45) Date of Patent: Jan. 3, 2006

(54) STENT BUMPER STRUTS

(75) Inventors: Brian J. Brown, Hanover, MN (US);
David M. Knapp, St. Paul, MN (US);
Jan Weber, Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 423 days.

(21) Appl. No.: 10/053,756

(22) Filed: Jan. 22, 2002

(65) Prior Publication Data

US 2003/0139798 A1 Jul. 24, 2003

(51) Int. Cl.
*A61F 2/06* (2006.01)
(52) U.S. Cl. ..................................... 623/1.15; 623/1.42
(58) Field of Classification Search ............... 623/1.15, 623/1.42–1.46, 1.1, 1.34
See application file for complete search history.

(56) References Cited

U.S. PATENT DOCUMENTS

| | | | |
|---|---|---|---|
| 4,503,569 A | 3/1985 | Dotter ............................ 3/1.4 |
| 4,512,338 A | 4/1985 | Balko et al. ................. 128/1 R |
| 4,732,152 A | 3/1988 | Wallsten et al. ............ 128/343 |
| 4,733,665 A | 3/1988 | Palmaz ........................ 128/343 |
| 4,768,507 A | 9/1988 | Fischell et al. .......... 128/303 R |
| 4,820,298 A | 4/1989 | Leveen et al. .................. 623/1 |
| 4,830,003 A | 5/1989 | Wolff et al. ................. 128/343 |
| 4,848,343 A | 7/1989 | Wallsten et al. ............ 128/343 |
| 4,886,062 A | 12/1989 | Wiktor ........................ 128/343 |
| 4,907,336 A | 3/1990 | Gianturco .................... 29/515 |
| 4,990,155 A | 2/1991 | Wilkoff ....................... 606/191 |
| 5,019,090 A | 5/1991 | Pinchuk ...................... 606/194 |
| 5,091,205 A | 2/1992 | Fan ............................... 427/2 |
| 5,234,456 A | 8/1993 | Silvestrini ................... 606/194 |
| 5,258,020 A | 11/1993 | Froix ............................. 623/1 |
| 5,443,458 A | 8/1995 | Eury ........................ 604/891.1 |
| 6,174,329 B1 * | 1/2001 | Callol et al. ................ 623/1.34 |
| 6,254,632 B1 * | 7/2001 | Wu et al. ................... 623/1.15 |
| 6,379,379 B1 * | 4/2002 | Wang ........................ 623/1.15 |
| 6,613,079 B1 * | 9/2003 | Wolinsky et al. .......... 623/1.15 |
| 2001/0044648 A1 | 11/2001 | Wolinsky et al. |

FOREIGN PATENT DOCUMENTS

| | | |
|---|---|---|
| CA | 2025626 | 9/1990 |
| CA | 2008312 | 5/2000 |
| EP | 1 025 812 A1 | 8/2000 |
| WO | 96/03092 | 2/1996 |
| WO | 98/02100 A1 | 1/1998 |
| WO | 99/39661 A2 | 8/1999 |

* cited by examiner

*Primary Examiner*—(Jackie) Tan-Uyen T. Ho
(74) *Attorney, Agent, or Firm*—Vidas, Arrett, Steinkraus

(57) ABSTRACT

A medical device comprises a stent having a reduced state and an expanded state and which is comprised of a plurality of interconnected struts. At least one strut is at least partially coated with a substance. The at least one strut has at least one bumper. The at least one bumper is constructed and arranged to prevent the substance on the at least one strut from being contacted by an adjacent component of the medical device when the stent is in the reduced state.

21 Claims, 8 Drawing Sheets

STENT BUMPER STRUTS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are generally tubular in configuration, open ended and are expandable between a generally unexpanded insertion diameter and an expanded implantation diameter. Stents are commonly placed or implanted by a mechanical transluminal procedure.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is concerned with balloon expandable stents, self expanding stents and/or hybrid stents.

An example of a stent is described in PCT Application NO. 960 3092 A1, published Feb. 8, 1996, the content of which is incorporated herein by reference.

U.S. Pat. Nos. 4,733,665; 5,019,090; 4,503,569; 4,512,338; describe various stent configurations. U.S. Pat. Nos. 4,732,152 and 4,848,343 describe self-expanding stents.

Stents have been made using materials of varied composition and conformation. U.S. Pat. No. 4,768,507 describes a stent constructed of stainless steel, and a titanium alloy. U.S. Pat. No. 4,820,298 describes a stent having a flexible tubular body made from a thermal plastic to the form of a helix. Polyester and polycarbonate copolymers are selected as particularly desirable materials. U.S. Pat. No. 4,830,003 describes a stent made from wires formed into a cylinder. The wires are made of a biocompatible metal. Biocompatible metals include 300 series stainless steels such as 316 LSS, as well as platinum and platinum iridium alloys, cobalt chromium alloys such as MP35N, and unalloyed titanium. U.S. Pat. No. 4,886,062 describes a stent made from low memory metal such as a copper alloy, titanium, or gold. U.S. Pat. No. 4,907,336 describes a wire stent having malleable materials such as annealed stainless steels, tungsten and platinum in its construction.

Canadian Application 2,025,626, describes a bio degradable infusion stent of extruded material. The stent may incorporate radiopaque materials such as barium sulfate. U.S. Pat. No. 4,990,155 describes a plastic stent having an inherently expandable coil conformation. Materials of construction include high density polyethylene. Optionally, this material is compounded with an anti coagulant and/or an x ray opaque material such as bismuth sub carbonate. Canadian Patent Application 2,008,312, describes a stent made from a malleable flat sheet having a reticulated pattern.

There are also stents which deliver agents or drugs to blood passing through the vein or artery that are generally beneficial to the recipient. In addition, stents can deliver drugs or biologically active agents at a controlled rate to blood passing through the vessel lumen as well as to the vessel wall. U.S. Pat. No. 5,234,456 describes a hydrophilic stent comprising a wall structure where at least a portion thereof is a hollow wall in which a hydrophilic material for drug delivery is placed. U.S. Pat. No. 5,443,458 is directed to a multilayer laminated resorbable stent having a structural layer and additional layers stated to release drugs at predictable rates. U.S. Pat. No. 5,258,020 describes a self-restrained stent with an elastic memory, the stent optionally being formulated to provide for drug administration.

Some medical devices such as stents may be provided with a coating. The coating may enhance or alter the performance characteristics of the medical device. In some cases the coating may be a drug, wherein the stent is used to deliver the drug coating directly to a location in a body lumen or vessel. A coating may be applied directly to a medical device or portion therein. Some devices include a reservoir or other feature which is specially designed to receive the drug and/or coating. In some cases a drug and/or coating may be applied to selected portions of a stent by masking features of the stent where it is undesired to provide the drug and/or coating.

It is known that in some cases, when stents are in the reduced state prior to delivery, components of the stent may be pressed together and may contact one another. Stent components may also come into external contact with various elements of a delivery catheter such as the catheter shaft, an external sheath, sleeve or sock, or other catheter components. Contact between stent components or contact between the stent and catheter components may result in a coating, particularly a drug coating, being broken off, rubbed away or otherwise impaired or damaged.

In some embodiments, the coating used on a stent, or a portion thereof, may be characterized as having a sticky or adhesive quality. When such a coating is present on stent components that may come into contact with one another, or when such coated components contact components of the catheter, the respective components may adhere or stick together with potentially detrimental effect to the stent, catheter, and/or the patient.

As a result, it is desired to provide a stent, or a portion of a stent with the capacity to be coated, wherein elements of such a coated stent are prevented from sticking together to ensure uniform expansion of the stent and to protect the drug coating from damage. It is further desired to provide a means for reducing or preventing contact between coated portions of a stent and other adjacent portions of the stent or potions of the delivery catheter or device.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

The present invention may be embodied in several forms. In at least one embodiment, the invention is directed to a stent having at least two struts. At least one of the struts has at least one member, hereinafter referred to as a bump or bumper, positioned thereon. A bumper is a member constructed and arranged to prevent, reduce or otherwise minimize contact between a strut body and other stent or medical device components when the stent is in a reduced configuration. In at least one embodiment a bumper is constructed and arranged to prevent, reduce or minimize contact between adjacent strut bodies. A bumper may be integral with a strut or may be a separate member attached to the strut body.

In some embodiments of the invention one or more of the struts may be coated. The coating may be comprised of one or more drugs or drugs in combination with one or more polymer complexes.

In some embodiments of the invention the at least one bumper prevents or reduces adherence between the body portions of adjacent struts when the stent is in the reduced configuration.

In some embodiments of the invention the at least one bumper protects a coating on at least a portion of the stent from being impaired or damaged. Preferably the at least one bumper reduces or prevents contact between the coated portion of a stent and adjacent stent or catheter components.

In some embodiments of the invention the stent comprises a plurality of strut pairs. Preferably, each strut pair comprises at least one bumper.

In at least one embodiment of the invention a stent comprises at least one bumper mounted on at least one external surface of a stent. The stent may include a drug coating. The at least one bumper is configured to reduce or prevent adherence between the stent and one or more catheter components adjacent to the stent in the reduced state. Where the stent includes a drug coating the at least one bumper prevents or reduces damage to the drug coating by reducing or preventing contact between the catheter components and the coated portion(s) of the stent.

Details of these and other embodiments of the invention are discussed below.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
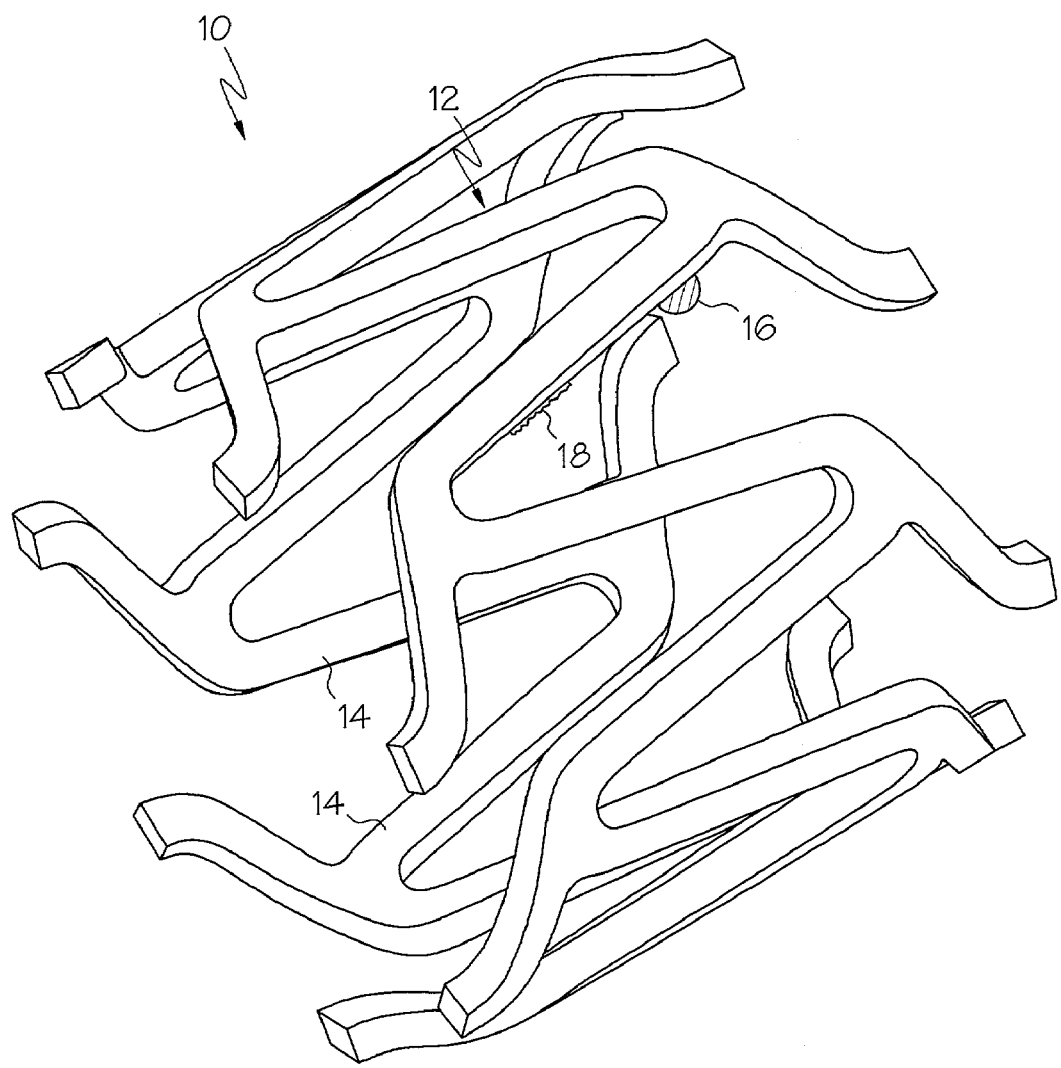
FIG. 1 is a perspective view of an embodiment of the invention.

Shown in FIG. 1 a partial view of a stent, indicated generally at 10, is illustrated in an expanded state. Stent 10, may be any kind of expandable prostheses such as a stent, stent-graft or graft. Stent 10 is a frame work of interconnected or interwoven members, referred to herein as struts 12. Struts 12, may be characterized as bridges, connecting members, support members, or any other element that is recognized as comprising the framework of a stent. Struts 12 may have shape size or configuration. For example, one or more struts may have straight, serpentine, sinusoidal, or other disposition or orientation.

In the present invention, at least one strut 12 of a stent 10, is equipped with a protrusion of material, characterized as a bump or bumper 16, which extends outward from at least a portion of the body 14 of the at least one strut 12. The bump 16 is constructed and arranged to reduce or prevent contact between the body 14 of adjacent struts 12 when the stent is in the reduced configuration shown in FIG. 3. In at least one embodiment, the bump 16 prevents the body 14 of adjacent struts 12 from contacting one another when the stent is in the reduced configuration shown.

In some embodiments of the invention a stent 10, or portion thereof, may be provided with a substance 18. Substance 18 may be a coating or a portion of the stent constructed and arranged to deliver the substance to a location in a body lumen. Substance 18 may be a drug, genetic material, cells, a non-genetic therapeutic agent, a polymer matrix having a therapeutic component or any other substance which it would desirable to deliver into a body lumen. In some embodiments the substance 18 may be a coating of SIBS (styrene isobutylene styrene); polycarboxylic acids; cellulosic polymers, including cellulose acetate and cellulose nitrate; gelatin, polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.); fibrin; collagen and derivatives thereof; polysaccharides such as celluloses, starches, dextrans, alginates and derivatives; hyaluronic acid; squalene emulsions; polyacrylic acid, available as HYDROPLUS® from Boston Scientific Corporation, Natick, Mass., and described in U.S. Pat. No. 5,091,205, the entire contents of which is hereby incorporated herein by reference.

Figure 15:
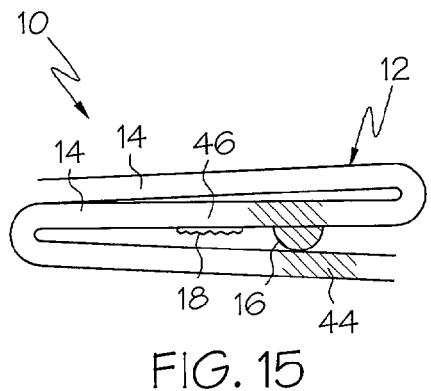
FIG. 15 is a partial side elevational view of an embodiment of the invention wherein a method of producing a stent is illustrated.

In some embodiment of the invention, proper placement of substance 18 on to a selected portion or portions of the stent, such as a strut body 14, is ensured through the use of a mask 44 such as may be seen in FIG. 15. In use, placement of a mask 44 allows for any and all portions of the stent 10 to be masked leaving exposed a portion or portions 46 of the stent 10 which is to be coated. Through the use of a mask 44, the substance 18 may be placed very precisely. Once the substance 18 is placed at the desired location 46 the mask is removed and the stent 10 is ready for use such as is show in FIGS. 1 and 3. Preferably, if a given strut 12 is to be coated with a substance 18, the bumper 16 and any strut portion which may be engaged thereto is masked to ensure that substance 18 is only minimally contacted by the bumper 16, or not contacted at all.

Figure 3:
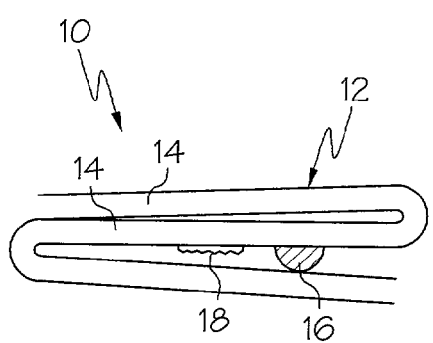
FIG. 3 is a partial side elevational view of the embodiment shown in FIG. 1 wherein adjacent struts of a stent are shown in the reduced state.

In the embodiment shown in FIGS. 1 and 3, a stent is shown having a single bumper 16 which prevents or reduces contact between the body 14 of adjacent struts 12. In the reduced state shown in FIG. 3, the bumper 16 may be engaged to a body 14 of a strut but the bumper 16 may be removed therefrom when the stent 10 is expanded to the expanded state shown in FIG. 1.

Figure 2:
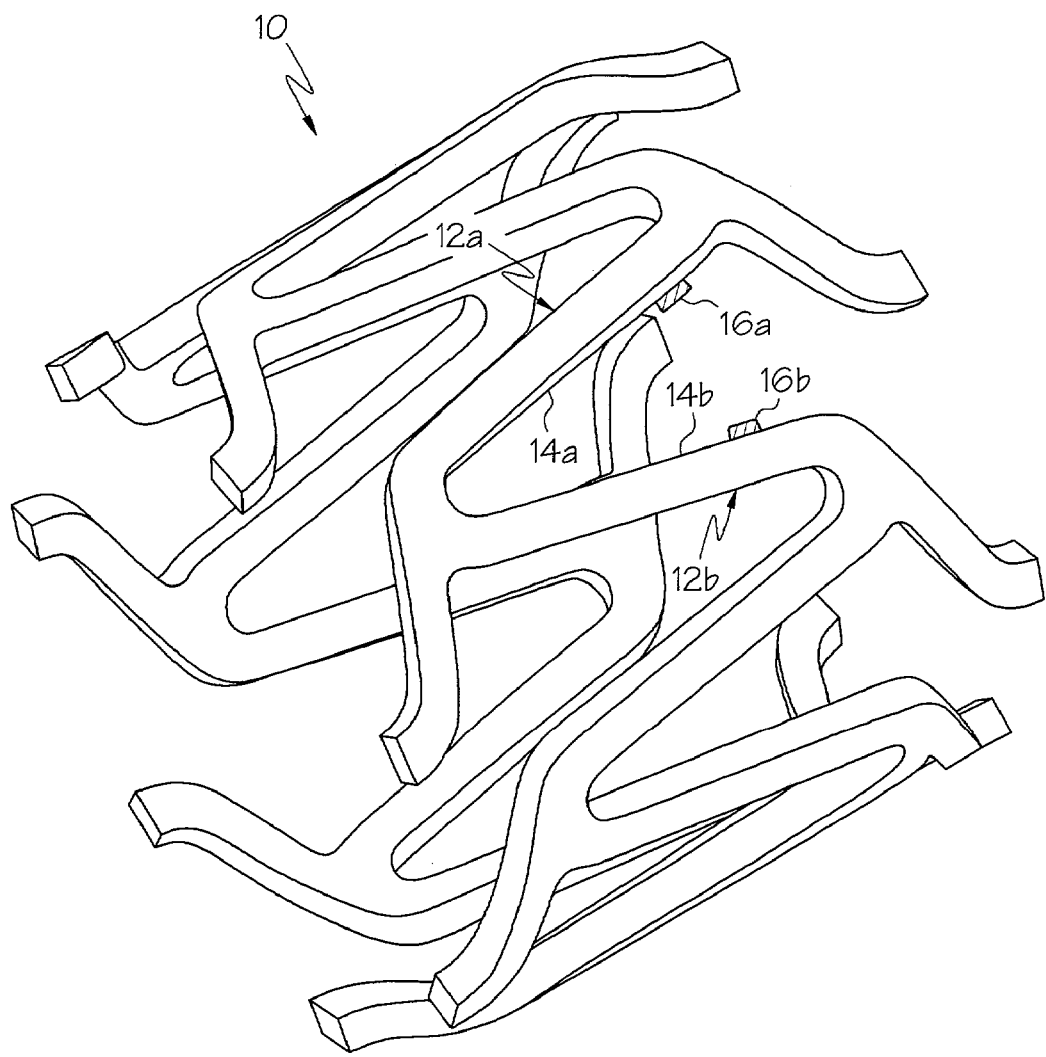
FIG. 2 is a perspective view of an embodiment of the invention.
Figure 4:
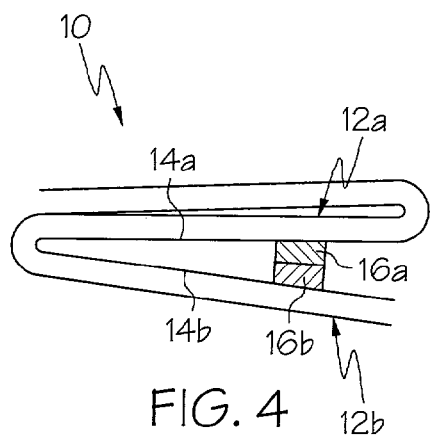
FIG. 4 is a partial side elevational view of the embodiment shown in FIG. 2 wherein adjacent struts of a stent are shown in the reduced state.
Figure 5:
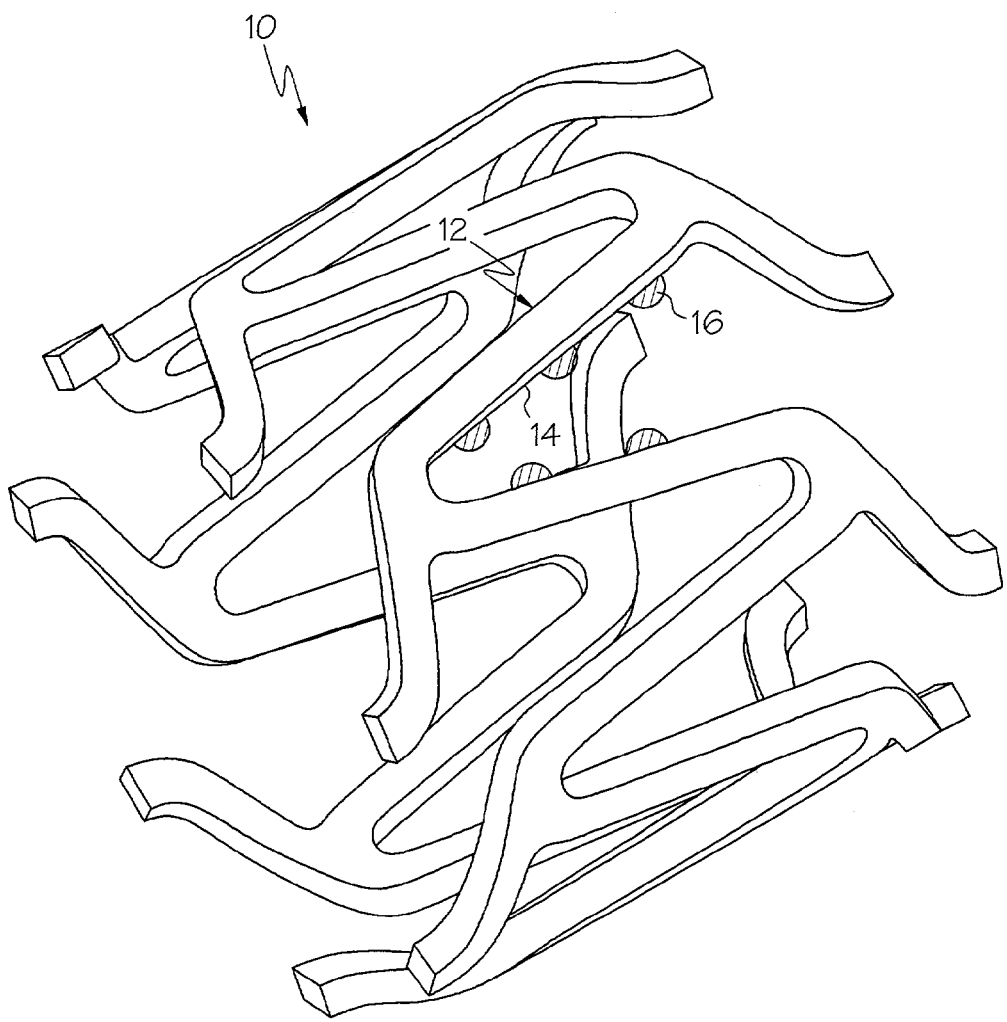
FIG. 5 is a perspective view of an embodiment of the invention.

In an alternative embodiment shown in FIG. 2, a pair of bumpers 16a and 16b may be positioned on opposing struts 12a and 12b. When the stent is in the reduced configuration shown in FIG. 4, the bumpers 16a and 16b may be configured to contact each other rather than to come into contact with the opposing body 14a and 14b of the respective struts 12a and 12b. Alternatively, where multiple bumpers 16 are utilized, such as in the embodiment shown in FIG. 5, the bumpers may be alternatingly placed along the strut body 14. The placement of the bumpers 16 relative to the strut 12 may be uniform or non-uniform as desired.

Figure 6:
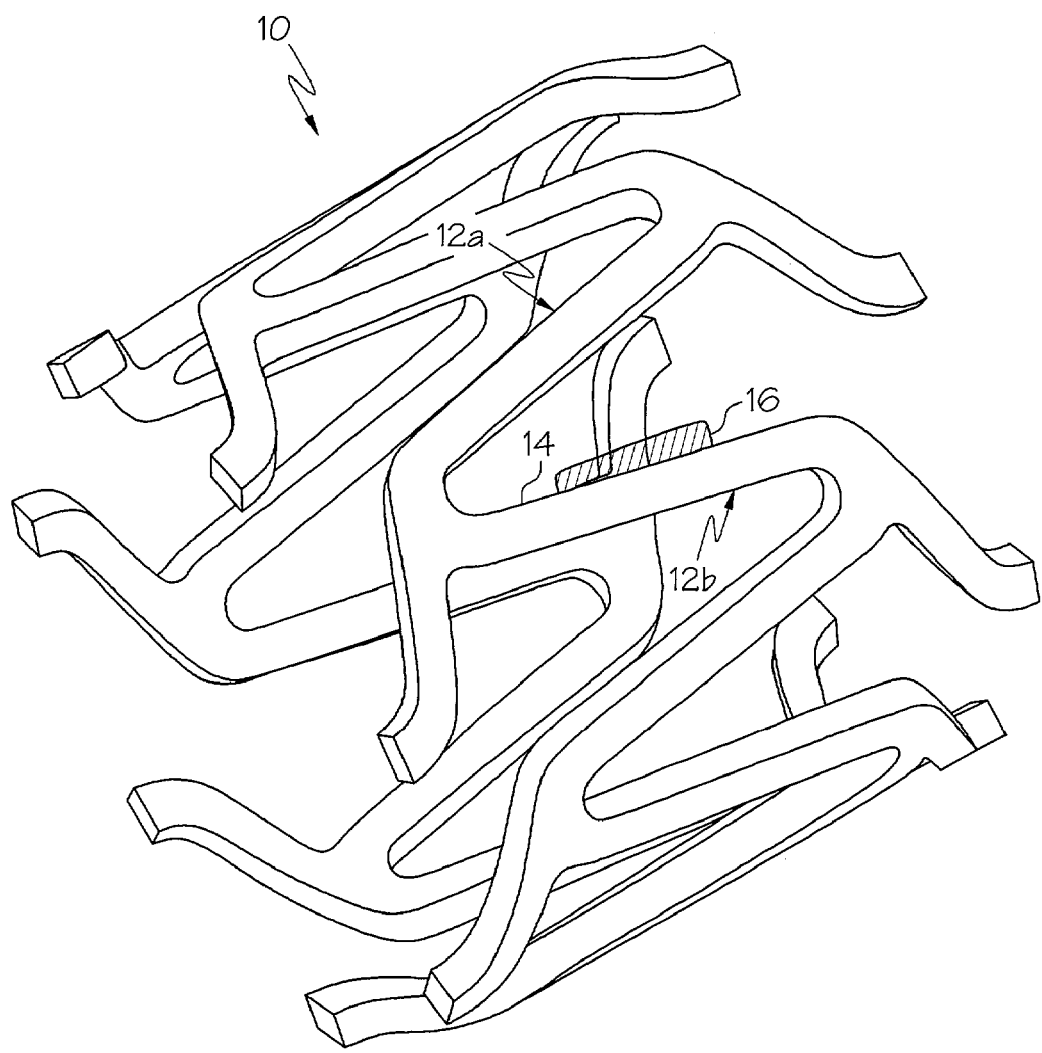
FIG. 6 is a perspective view of an embodiment of the invention.

Not only may the bumpers 16 be placed in any manner along a given strut or struts 12, individual bumpers 16 may be provided with a wide range of shapes, sizes, configurations, and compositions. For example, in the embodiment shown in FIG. 6, a single bumper is shown having an elongate shape which tapers in height from end to end. The unique shape of the bumper 16 accommodates the shape of the stent in the reduced state and may provide improved separation between strut 12a and 12b.

Figure 7:
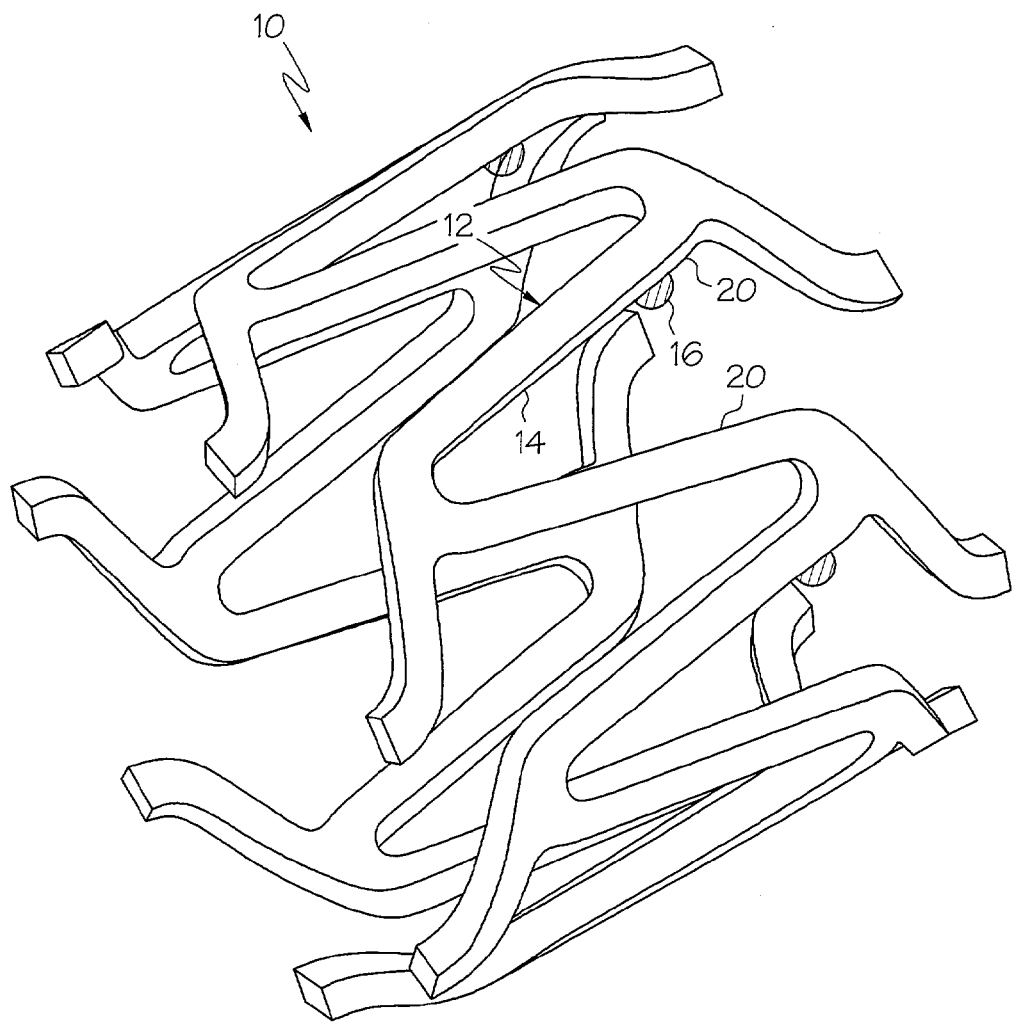
FIG. 7 is a perspective view of an embodiment of the invention.

In the various embodiments which comprise the present invention, the bumpers 16 may be constructed from any material desired. Because stents are utilized within the human body, the bumpers 16 are preferably constructed of a biocompatible material or materials. Where the bumper 16 includes a non-biocompatible material in its construction the bumper 16 preferably includes a biocompatible coating. Preferably, the bumper is constructed out of the same material as the strut 12 which the bumper 16 extends from. The bumper 16 may be an inherent part of the strut 12, being merely a protrusion of strut material, or it may be a separate component which is welded, adhered, or otherwise engaged to the strut 12. A bumper 16 may be positioned anywhere along or about the body 14 of a strut 12. In at least one embodiment illustrated in FIG. 7, the body 14 of at least one strut 12 of each strut pair 20 includes at least one bumper 16 to provide separation between the respective bodies 14 of a given strut pair 20.

Figure 8:
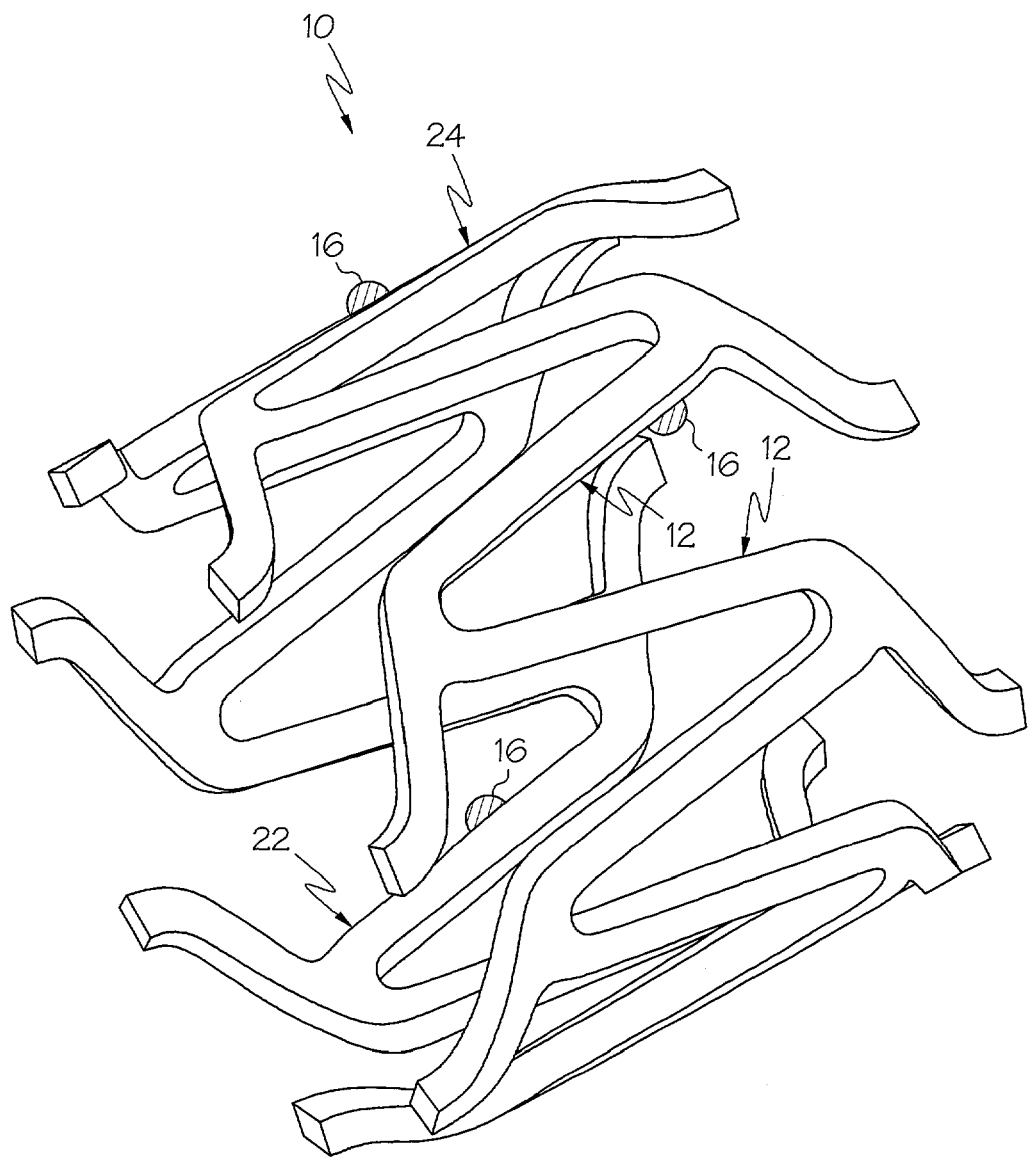
FIG. 8 is a perspective view of an embodiment of the invention.

As suggested above one purpose for providing a stent 10 with bumpers 16, such as have been discussed thus far, is to prevent or reduce contact between the bodies 14 of adjacent struts 12 when the stent is in the reduced state. However, as may be seen in FIG. 8 the stent 10 may also be provided with externally protruding bumpers 16 which may protrude from either the inside surface 22 or the outside surface 24 of a given strut 12.

Figure 9:
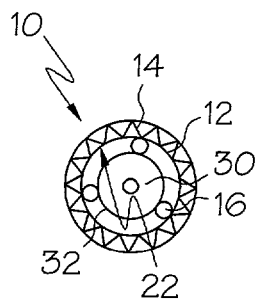
FIG. 9 is a cross-sectional view of an embodiment of the invention wherein a stent having internally mounted bumpers on the inside radial surface of the stent is shown mounted on a stent delivery catheter.

When the stent 10, is mounted onto a stent delivery catheter 30, such as in the embodiment shown in FIG. 9, a bumper(s) 16 which protrudes from the inside surface 22 of a strut 12, may provide the stent 10 with protection from adverse contact between a strut body 14 and a portion of a catheter 30 such as a inflation balloon or shaft 32.

Figure 10:
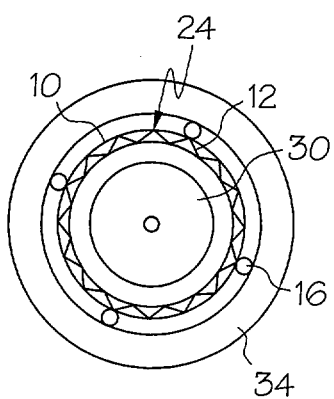
FIG. 10 is a cross-sectional view of an embodiment of the invention wherein a stent having bumpers on the outside radial surface of the stent is mounted on a stent delivery catheter.

In the embodiment shown in FIG. 10, where bumpers 16 protrude from the outside surface 24 of a strut 12, the bumpers may be used to provide the strut body 14 with protection from adverse contact with a retaining member 34 such as a sheath, sleeve, or sock.

Figure 11:
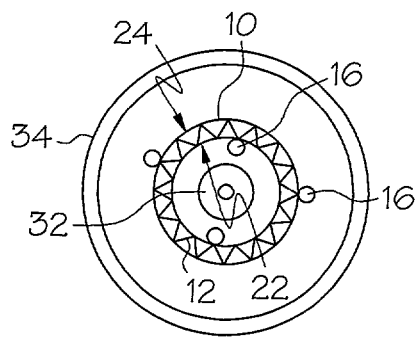
FIG. 11 is a cross-sectional view of an embodiment of the invention wherein a stent having bumpers on the inside radial surface and outside radial surface is shown mounted on a stent delivery catheter.

In another embodiment, shown in FIG. 11 a stent 10 may be provided with one or more bumpers 16 which externally protrude from the inside surface 22 and outside surface 24 of the same or different struts 12. In this manner the stent 10 is protected from adverse contact between the balloon or mounting shaft 32 and the inside surface 22 of struts 12, as well as between the outside surface 24 of the struts 12 and the retaining member 34.

In any of the embodiments shown or described, a stent may be provided with one or more bumpers to prevent or reduce contact between adjacent struts. Likewise, in any of the embodiments shown or described, the stent may be provided with bumpers which protrude from the inside and/or outside strut surfaces.

Depending on the flexibility of the stent as well as of the catheter, the bumpers in the various embodiments of the present invention, may be provided with a wide range of heights or thicknesses relative to the strut 12 from which the bumpers extend. The bumpers may extend from about 0.0002 inches to about 0.015 inches from a given strut 12. Preferably, the bumpers 16 extend from a strut 12 by about 0.0002 to about 0.015 inches. These values may be significantly reduced where multiple bumpers are configured to engage one another such as in the embodiments shown in FIGS. 2 and 4.

Figure 12:
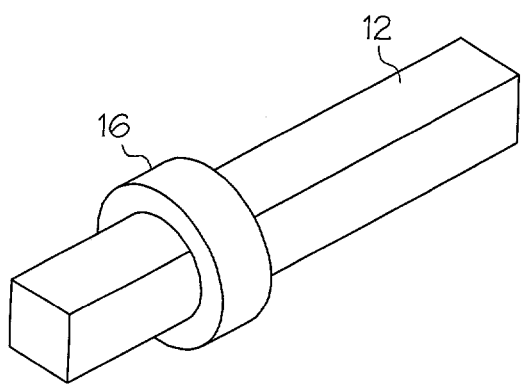
FIG. 12 is a perspective view of an embodiment of the invention.

In the various embodiments shown in FIGS. 1–11, the bumpers 16 have been shown to provide separation between components in only one direction. It must be noted however, that the bumpers may be configured to protrude from a given strut 12 to provide separation in more than one direction. For example, a strut 12 may be provided with a bumper 16 that is disposed about the strut 12 in the manner shown in FIG. 12. The bumper 16 may be characterized as a ring, or sheath, which surrounds at least a portion of the bumper body 14. In this manner, bumper 16 may provide the strut with protection from adverse contact from adjacent struts, radially external catheter components, and radially inward catheter components as well. Preferably, such a ring like bumper 16 has a uniform thickness around the strut 12. However, depending on the particular catheter design with which the stent is to be used, the thickness of the bumper 16 may be varied in any direction relative to the strut 12. The bumper 16 may completely surround a portion of the strut 12 as shown, or alternatively may partially surround the strut 12 in any manner desired.

Figure 13:
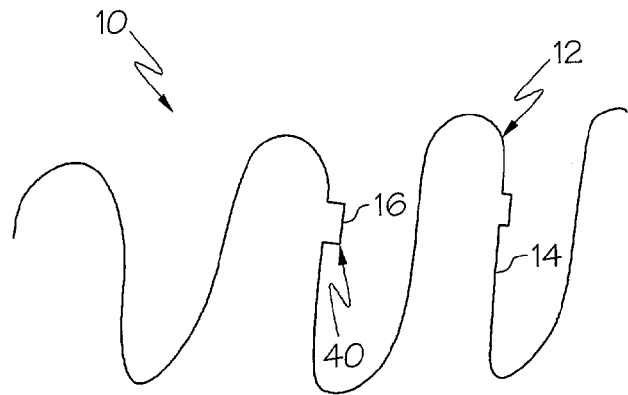
FIG. 13 is a side elevational view of an embodiment of the invention.
Figure 14:
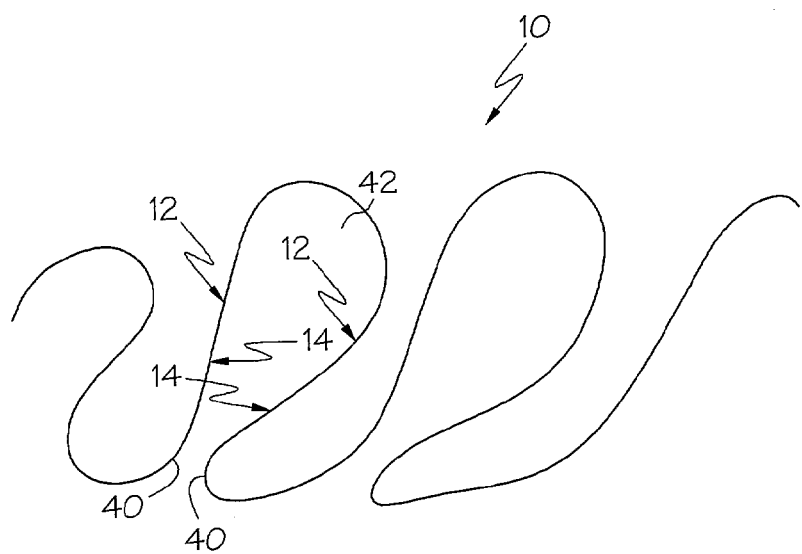
FIG. 14 is a side elevational view of an embodiment of the invention.

In yet another embodiment of the invention shown in FIG. 13, the stent 10 may include struts 12 which have one or more bends, distortions, or other portions 40 which act as a bumper 16, to reduce prevent or otherwise minimize contact between adjacent strut bodies 14. When in the reduced state the portions 40 and adjacent bodies 14 share a common plane thereby ensuring that the bodies 14 of the adjacent struts 12 are not contacted or only minimally contacted. In yet another embodiment, an example of which is shown in FIG. 14, the stent 10 may include adjacent struts 12 which define loops 42. The loops 42 are provided with shapes such that a portion 40 engages a portion 40 of adjacent struts 12. In at least one embodiment, the design of the stent 10 may include struts 12 which are aligned such that adjacent struts 12 have a minimal amount of contact with each other. As a result, in the reduced state the most or all of the adjacent strut bodies 14 will be in minimal contact or have no contact at all.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

We claim:

1. A medical device comprising:
    a stent, the stent having a reduced stale and an expanded state and being comprised of a plurality of interconnected struts, the stent being coated with a polymer matrix, the polymer matrix of at least one strut comprising a therapeutic substance, at least one strut having at least one bumper, in the reduced state the at least one bumper being immediately adjacent to the at least one strut comprising the therapeutic substance but not in contact with the therapeutic substance.

2. The medical device of claim 1 wherein the at least one strut at least partially coated with a therapeutic substance and the at least one strut having at least one bumper are the same strut.

3. The medical device of claim 1 wherein the plurality of interconnected struts comprise at least one strut pair, the at least one strut pair having at least one bumper thereon.

4. The medical device of claim 3 wherein at least one pair of adjacent struts have bumpers facing one another.

5. The medical device of claim 4 wherein the bumpers facing one another are constructed and arranged to removably engage each other when the stent is in the reduced state.

6. The medical device of claim 4 wherein the at least one pair of adjacent struts have a plurality of bumpers facing one another.

7. The medical device of claim 6 wherein the plurality of bumpers facing one another are constructed and arranged to removably engage an opposing strut of the at least one pair of adjacent struts.

8. The medical device of claim 1 wherein the at least one strut having at least one bumper has a strut length, the at least one bumper having a bumper length, the bumper length being less than about half of the strut length.

9. The medical device of claim 1 wherein the at least one strut having at least one bumper has a strut length, the at least one bumper having a bumper length, the bumper length being at least about half of the strut length.

10. The medical device of claim 1 wherein the at least one bumper has a bumper height and a bumper length, the bumper height varying along the bumper length.

11. The medical device of claim 1 wherein the at least one strut having at least one bumper comprises a plurality of surfaces, the at least one bumper protruding from at least one of the plurality of surfaces.

12. The medical device of claim 11 wherein the plurality of surfaces comprise an inside facing surface, an outside facing surface, and at least one surface facing the plane of the stent.

13. The medical device of claim 12 wherein the at least one bumper protrudes from the inside facing surface.

14. The medical device of claim 12 wherein the at least one bumper protrudes from the outside facing surface.

15. The medical device of claim 12 wherein the at least one bumper protrudes from the at least one surface facing the plane of the stent.

16. The medical device of claim 11 wherein the at least one bumper protrudes from each of the plurality of surfaces.

17. The medical device of claim 16 wherein the at least one bumper is disposed about at least a portion of the at least one strut having at least one bumper.

18. The medical device of claim 1 wherein the therapeutic substance is selected from at least one member of the group consisting of a drug, genetic material, cells, a non-genetic therapeutic agent, and any combination thereof.

19. The medical device of claim 1 wherein the polymer matrix is selected from at least one member of the group consisting of SIBS (styrene isobutylene styrene); polycarboxylic acid; cellulosic polymer, such as cellulose acetate and cellulose nitrate; gelatin, polyvinylpyrrolidone; crosslinked polyvinylpyrrolidone; polyanhydride such as maleic anhydride polymer; polyamide; polyvinyl alcohol; copolymers of vinyl monomers such as EVA; polyvinyl ether; polyvinyl aromatic; polyethylene oxide; glycosaminoglycan; polysaccharide; polyesters such as polyethylene terephthalate; polyacrylamide; polyether; polyether sulfone; polycarbonate; polyalkylenes including polypropylene, polyethylene and high molecular weight polyethylene; halogenated polyalkylenes such as polytetrafluoroethylene; polyurethane; polyorthoester; protein; polypeptide; silicone; siloxane polymer; polylactic acid; polyglycolic acid; polycaprolactone; polyhydroxybutyrate valerate and blends and copolymers thereof; polyurethane dispersions; fibrin; collagen and derivatives thereof; polysaccharides such as celluloses, starches, dextrans, alginates and derivatives; hyaluronic acid; squalene emulsion; polyacrylic acid and any combinations thereof.

20. A method of producing a stent comprising:

providing a stent having a reduced state and an expanded state and being comprised of a plurality of interconnected struts, the stent being coated with polymer matrix, at least one of the struts having a strut body and at least one bumper, the at least one bumper constructed and arranged to reduce or prevent contact between the strut body and an adjacent strut of stent when the stent is in the reduced state;

placing a mask about at least a portion of the stent, thereby providing at least one exposed portion and at least one masked portion;

placing a therapeutic substance on the at least one exposed portion;

removing the mask.

21. The method of claim 20 wherein the at least one masked portion includes the at least one bumper or a portion of a strut adjacent thereto.

* * * * *